United States Patent [19]
Sawers et al.

[11] Patent Number: 5,834,009
[45] Date of Patent: Nov. 10, 1998

[54] CONTOURED ADHESIVE WAFER FOR OSTOMY APPLIANCE

[75] Inventors: Michael F. Sawers, Oxfordshire, England; Thomas H. Gilman, Spring Grove, Ill.; Barry L. Schneider, McHenry, Ill.; Eric D. Ellingson, Mount Prospect, Ill.; Ronald S. Botten, Gurnee, Ill.; Werner E. Engelmann, Arlington Heights, Ill.

[73] Assignee: Hollister Incorporated, Libertyville, Ill.

[21] Appl. No.: 963,316

[22] Filed: Nov. 3, 1997

Related U.S. Application Data

[60] Division of Ser. No. 718,955, Sep. 26, 1996, Pat. No. 5,730,736, which is a continuation-in-part of Ser. No. 640,008, Apr. 30, 1996.

[51] Int. Cl.⁶ .............................. A61L 15/16; A61F 5/44
[52] U.S. Cl. ........................ 424/443; 424/444; 424/445; 424/446; 604/332; 604/336; 604/337; 604/338; 604/339; 604/342; 604/344
[58] Field of Search ..................... 604/332, 336, 604/337, 338, 339, 342, 344; 424/443, 444, 445, 446

[56] References Cited

U.S. PATENT DOCUMENTS

| | | | |
|---|---|---|---|
| 3,081,771 | 3/1963 | Lee | 128/283 |
| 3,457,919 | 7/1969 | Harbard | 128/156 |
| 3,941,133 | 3/1976 | Chen | 128/283 |
| 4,341,207 | 7/1982 | Steer et al. | 128/155 |
| 4,699,792 | 10/1987 | Nick et al. | 424/446 |
| 4,773,408 | 9/1988 | Cilento et al. | 128/156 |
| 4,921,704 | 5/1990 | Fabo | 424/446 |
| 4,995,382 | 2/1991 | Lang et al. | 128/156 |
| 5,051,259 | 9/1991 | Olsen et al. | 424/443 |
| 5,123,900 | 6/1992 | Wick | 602/41 |
| 5,244,457 | 9/1993 | Karami et al. | 602/55 |
| 5,496,296 | 3/1996 | Holmberg | 604/336 |
| 5,501,678 | 3/1996 | Olsen | 604/344 |
| 5,567,488 | 10/1996 | Allen et al. | 604/332 |
| 5,609,585 | 3/1997 | Botten et al. | 604/332 |
| 5,730,736 | 3/1998 | Sawers et al. | 604/344 |

FOREIGN PATENT DOCUMENTS

| | | |
|---|---|---|
| 0 353 972A | 2/1990 | European Pat. Off. . |
| 0 409 587A | 1/1991 | European Pat. Off. . |
| 2 283 916 | 5/1995 | United Kingdom . |
| 89/05619 | 6/1989 | WIPO . |
| 91/01706 | 2/1991 | WIPO . |
| 94/15562 | 7/1994 | WIPO . |

*Primary Examiner*—Thurman K. Page
*Assistant Examiner*—Kathryne E. Shelborne
*Attorney, Agent, or Firm*—Tilton Fallon Lungmus

[57] ABSTRACT

An adhesive wafer for an ostomy pouch, and the combination of such a wafer and pouch, in which the adhesive layer of the wafer is composed of a hydrocolloid-containing skin barrier material and is contoured to provide a relatively thick body portion surrounded by a relatively thin peripheral portion, are disclosed. The wafer has a stoma-receiving opening, and the adhesive layer is of developed shape so that most, if not all, of the relatively thick body portion is located immediately below and to the sides of the stoma-receiving opening. The relatively thin peripheral portion of the adhesive layer is preferably embossed to provide a pattern of discrete, non-connecting depressions separated and isolated from each other by flat-top ridges dimensioned and arranged so that a skin surface engaged by said embossed surface primarily contacts only such ridges.

13 Claims, 2 Drawing Sheets

CONTOURED ADHESIVE WAFER FOR OSTOMY APPLIANCE

RELATED APPLICATION

This application is a division of application Ser. No. 08/718,955, filed Sep. 26, 1996, now U.S. Pat. No. 5,730,736, which is a continuation-in-part of copending application Ser. No. 08/640,008, filed Apr. 30, 1996.

BACKGROUND AND SUMMARY

Adhesive wafers in which the adhesive material has hydrocolloid particles dispersed therein, and is moisture absorbing as well as providing both dry and wet tack, are well known for use as wound dressings and as the attachment faceplates for ostomy appliances. When used as the faceplate for an ostomy appliance, such a wafer is provided with a stoma-receiving opening and has a backing layer that is secured either permanently or detachably to a collection pouch for receiving stomal discharge. The hydrocolloid-containing adhesive layer, commonly referred to as being composed of skin barrier material, is intended to maintain a liquid-tight seal against peristomal skin surfaces to prevent leakage of waste material and protect such skin surfaces from the excoriating effect of digestive fluids. In ileostomy cases where the stomal discharge is from the small intestine, the digestive liquids are still active and are capable of serious injury to skin surfaces unless such surfaces are adequately protected by the soft adhesive barrier material.

The period of time such an adhesive wafer may remain in contact with the skin before being replaced by a fresh wafer depends in part on the rate in which the barrier material becomes hydrated and degraded by contact with stomal fluid. Other things being equal, an adhesive layer that is relatively thick might be expected to degrade more slowly and provide a longer duration of protection against leakage and possible injury to the wearer's skin. However, it is also known that a wafer in which the adhesive material is too thick may be incapable of conforming with anatomical contours, and of changes in such contours as a patient moves about, creating the possibility that channels may develop between the wafer and the skin and leakage may result. To reduce or eliminate such possibilities, wafers are now made in a contoured configuration with the adhesive material immediately surrounding the stoma-receiving opening being relatively thick and then tapering outwardly into a relatively thin peripheral flange portion that will remain sealed to the skin even after periods of vigorous wearer movement.

In our copending application, we disclose a contoured wafer in which the adhesive material of the outer flange portion is embossed in such a way as to limit the extent of surface contact with the skin and, even more significantly, to render it unlikely that the same skin surfaces will be contacted to the same extent when the wafer is removed and replaced by a fresh wafer. Specifically, the bodyside surface of the wafer's adhesive layer is embossed to provide a pattern of small, discrete, non-connecting depressions or recesses separated and isolated from each other by flat-top skin-contacting ridges. When the wafer is in place, skin surfaces engaged by the embossed surface primarily contact only the ridges. The pattern of embossing renders it highly unlikely that only the skin areas contacted by a removed wafer will again be contacted by a fresh replacement wafer, since even slight lateral or rotational displacement in the position of the fresh wafer will bring its ridges into adhesive contact with skin surfaces not engaged by the previous wafer. The result is a wafer of enhanced skin friendliness which promotes healing, or at least avoids or reduces irritation, of the isolated skin areas underlying the depressions and which eliminates or reduces the possibilities that surface layers of skin will be stripped away as an adhesive wafer is removed.

An important aspect of the present invention lies in the discovery that the effectiveness of an adhesive wafer may be further enhanced if the increased thickness of barrier material is provided in certain locations where it is needed most, allowing for more barrier material to be located where fluid exposure is expected to be substantial and less barrier material in those areas where such exposure is expected to be relatively slight. The result is a contoured wafer in which the adhesive material of greater thickness is found principally beneath and to the sides of the stoma-receiving opening.

The body portion of greater barrier thickness may extend completely around the stoma-receiving opening, but with a greater mass of barrier material located below and to the sides of that opening, or it may assume a crescent shape so that the greater thickness is found only below and to the sides of the opening. In either case, in a circular area of reference concentric with the stoma-receiving opening, the quantity of barrier material in the semicircular lower half of that reference area exceeds the quantity in the upper half because of the differences in barrier thickness.

By concentrating the barrier material of greater thickness in critical areas, a wafer embodying the invention having the same amount of relatively expensive barrier material as a conventional wafer can be expected to have increased effectiveness in terms of skin protection and leakage prevention. By embossing the relatively thin outer peripheral portion of the adhesive layer, material costs are additionally reduced while providing increased skin friendliness because of the unlikelihood that only skin areas contacted by a removed wafer will again be contacted by a replacement wafer.

Other features, advantages, and objects of the invention will become apparent from the specification and drawings.

DRAWINGS

DETAILED DESCRIPTION OF PREFERRED EMBODIMENTS

Figure 1:
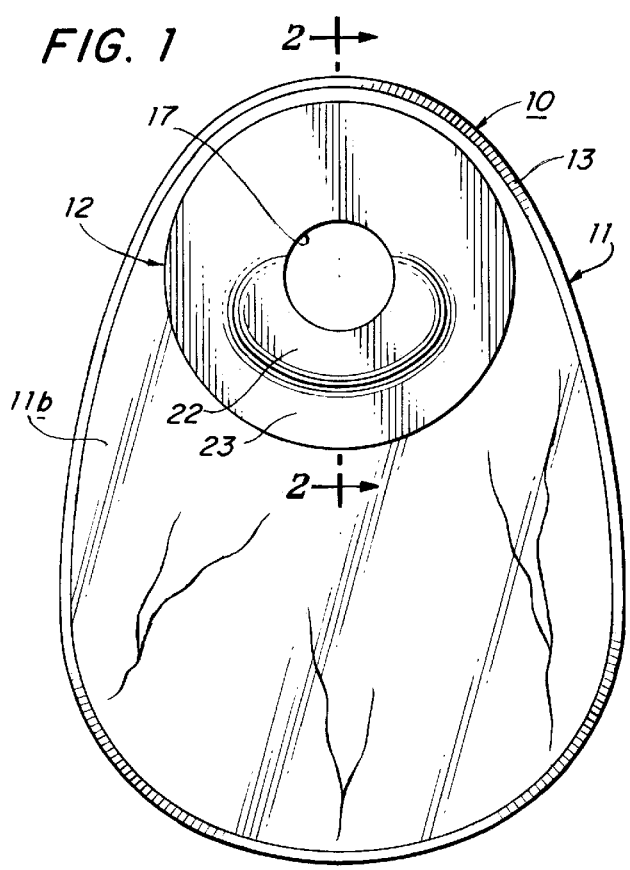
FIG. 1 is a rear elevational view of an ostomy appliance embodying the invention.
Figure 2:
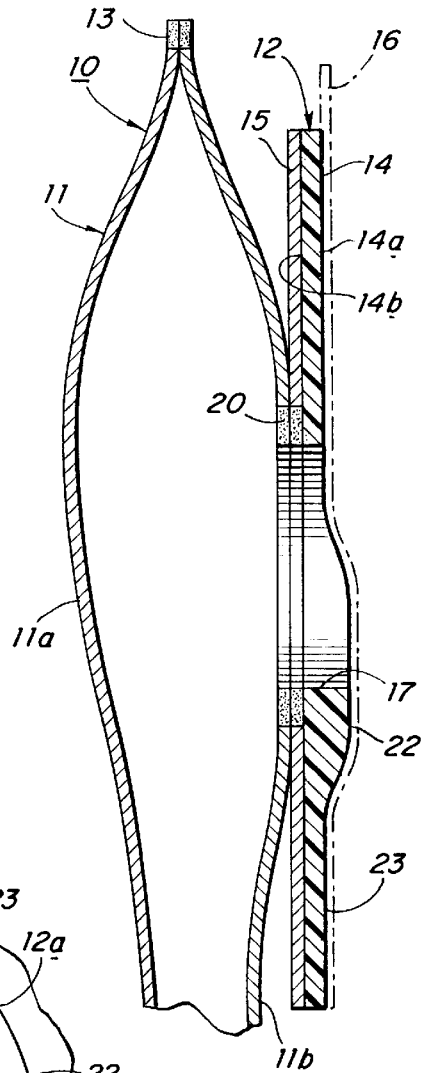
FIG. 2 is an enlarged sectional view taken along line 2—2 of FIG. 1.
Figure 3:
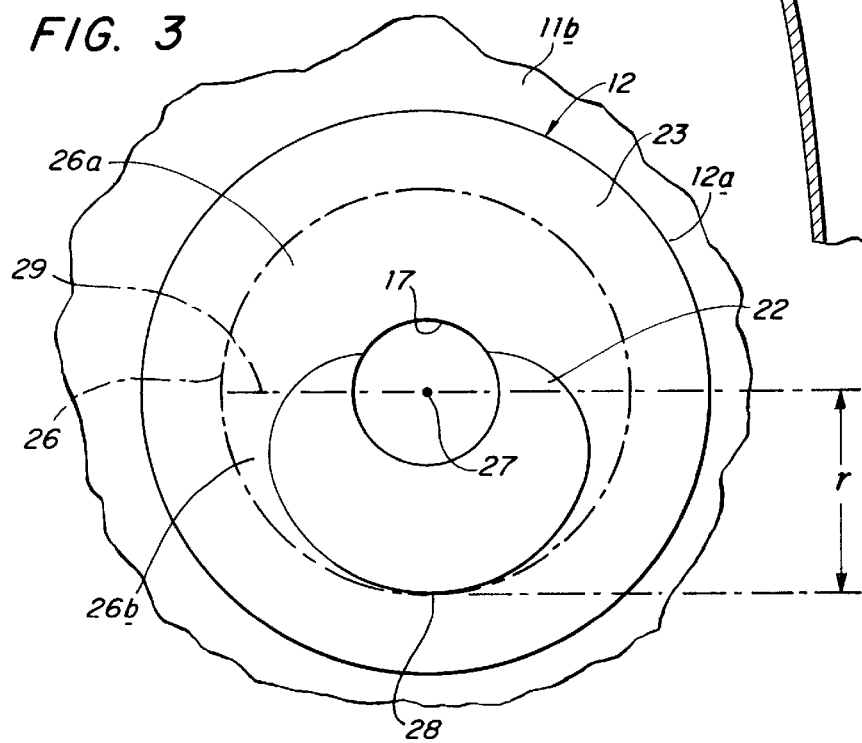
FIG. 3 is an enlarged fragmentary elevational view illustrating the bodyside face of the wafer in relation to a circle of reference.

Referring to FIGS. 1–3 of the drawings, the numeral 10 generally designates an ostomy appliance comprising a pouch 11 and an adhesive wafer 12 serving as the faceplate for adhesively attaching the appliance to the peristomal skin surfaces of a patient. The pouch 11 is conventional, being essentially composed of a pair of side walls 11*a* and 11*b* of thermoplastic film sealed to each other along their edges 13. While the pouch is shown as being heat sealed along all of its edges, it may optionally be provided with a drainage opening at its lower end. Such opening, if provided, may be closed by a suitable clamp of the type disclosed in U.S. Pat. No. 3,523,534 or, alternatively, may be equipped with a valve as disclosed, for example, in U.S. Pat. Nos. 3,598,150 and 4,280,498. The pouch may be formed of a film composed of any suitable heat-sealable plastic or combination of plastics (e.g., as a coextruded laminate) that is tough, flexible, and liquid and gas impermeable, all as well known in the art. One such film found to be particularly effective is a coextrusion of polyethylene and polyvinylidene chloride available under the trademark "Saranex" from Dow Chemical, Midland, Mich., but other films having similar properties may be used.

Wafer 12 is in the form of a disc which is illustrated in FIG. 1 as being generally circular in shape but, if desired, other configurations may be selected. As shown in FIG. 2, the wafer essentially comprises an occlusive adhesive layer 14 and a backing layer 15. The adhesive layer is generally planar and has a rear or bodyside surface 14a and a front or pouchside surface 14b. The flexible backing layer 15 covers the pouchside surface 14b and a removable release sheet 16 composed of siliconized paper, silicone-coated plastic, or other material which resists strong adherence to the adhesive material, covers surface 14a (the release sheet is shown only in phantom in FIG. 2). A stoma-receiving opening 17 extends through layers 14 and 15 and may be pre-sized to fit the patient or, alternatively, may be provided as a starter opening capable of being enlarged by the user (with scissors) to provide a re-formed opening that is sized and configured to match the patient's stoma.

Backing layer 15 must be flexible and may also be stretchable and contractable for purposes of anatomical conformity. It may be in the form of a film of polyurethane, polyethylene, or other suitable thermoplastic material. Alternatively, it may be a soft, flexible thermoplastic foam of closed, semi-open, or fully-open cell construction. Polyurethane or polyethylene foams are believed suitable, but other thermoplastic foams having similar properties may be used. Particularly effective results are obtained where the backing layer 15 is gas pervious and formed of a soft, porous non-woven fabric of thermoplastic fibers such as, for example, a non-woven fabric of spun-bonded polyethylene fibers. One such fabric is marketed under the designation P80-00 by Corovin GmBh, Peine, Germany, but other non-woven fabrics having similar properties may be used. The backing layer 15 is permanently joined to wall 11b of the pouch by one or more annular heat seals 20 surrounding the stoma-receiving opening 17.

Adhesive layer 14 is a moisture-absorbing and moisture-swellable skin barrier material having a continuous phase composed of one or more tacky elastomers and a discontinuous phase consisting essentially of particles of one or more hydrocolloids dispersed throughout the adhesive layer. Typical hydrocolloids are pectin, gelatin and sodium or calcium carboxymethylcellulose, but other hydrocolloids such as karaya may be used. If desired, superabsorbents may be included in the skin barrier formulation. The continuous elastomeric phase may be composed of a tacky, deformable elastomeric material such as polyisobutylene and/or a block copolymer such as a styrene-isoprene-styrene copolymer of the type described in U.S. Pat. Nos. 4,738,257 and 4,231,369. Tackifiers, plasticizers, extenders and stabilizers may be included, all as well known in the art.

A characteristic feature of wafer 12 lies in the fact that it is contoured to provide a relatively thick body portion 22 adjacent stoma-receiving opening 17 and a relatively thin peripheral portion 23. In the drawings, the contouring is shown along only the bodyside surface 14a with the pouchside surface 14b being relatively flat or planar; however, if desired, the contouring may be provided along both surfaces or, in some cases, along only the pouchside surface. Thickness dimensions of the body and peripheral portions may be varied considerably depending on factors such as the particular barrier formulation selected and the expected wear time for such a wafer but, in general, the thickness of the peripheral portion should be less than 0.5 mm, preferably no more than 0.3 mm, and the body portion should have a thickness more than 0.5 mm, and preferably 1.0 mm or more. The thinness of the peripheral portion allows the adhesive barrier material to conform to folds and irregularities in skin surfaces and to remain in sealing contact with such surfaces as a patient moves about, whereas the relatively thick body portion functions to maintain a soft, pliant, liquid-tight seal about the patient's stoma.

Body portion 22 is located at the edge of stoma opening 17 and may, if desired, extends completely about that opening. In the embodiment illustrated, the thick body portion 22 is somewhat crescent-shaped and extends only beneath and to the sides of opening 17. Whether the thick body portion surrounds the opening or extends only beneath and to the sides of that opening, a greater quantity of adhesive barrier material is located beneath the opening than above it. The result is an adhesive wafer in which the greater thickness of skin barrier material is concentrated in the areas of the wafer where it is needed most. With an ostomy pouch worn in the orientation depicted in the drawings, fluids discharged into the pouch through stoma opening 17 tend because of gravitational influences to make greater contact with the barrier material exposed along the lower edges of opening 17. The rate of hydration of the barrier material along the lower portions of the opening also tends to be greater but, because a greater quantity of absorbent barrier material is concentrated in that location, such hydration may proceed with less risk of leakage and with the possibilities of longer wear time for a wafer having the same amount of barrier material as a conventional wafer.

The greater quantity of barrier material located immediately beneath and to the sides of opening 17 may be best understood from FIG. 3. Stoma opening 17 is shown to be concentric with the outer edge 12a of wafer 12 although, if desired, the opening may be slightly above (or even below) center and the wafer may be non-circular in outline. Phantom line 26 defines a circular area of reference that is concentric with stoma opening 17. The radius "r" of the circular area of reference 26 is equal to the distance from the center 27 of the opening to the lowermost limits 28 of the relatively thick body portion 22. As shown in FIG. 3, the circular area of reference 26 is divided by line 29 into upper and lower halves 26a and 26b of equal area. A fundamental aspect of this wafer construction is that the quantity of skin barrier material in the lower half 26b is substantially greater than the quantity in upper half 26a. By "substantially" is meant that the quantity of skin barrier material in the lower half 26b of the circular zone of reference 26 is at least 10% more, and preferably at least 30% more, than in the upper half 26a. Such is the case regardless of whether the relatively thick body portion of barrier material extends completely about opening 27 or only below and to the sides of that opening as depicted in the drawings.

Figure 4:
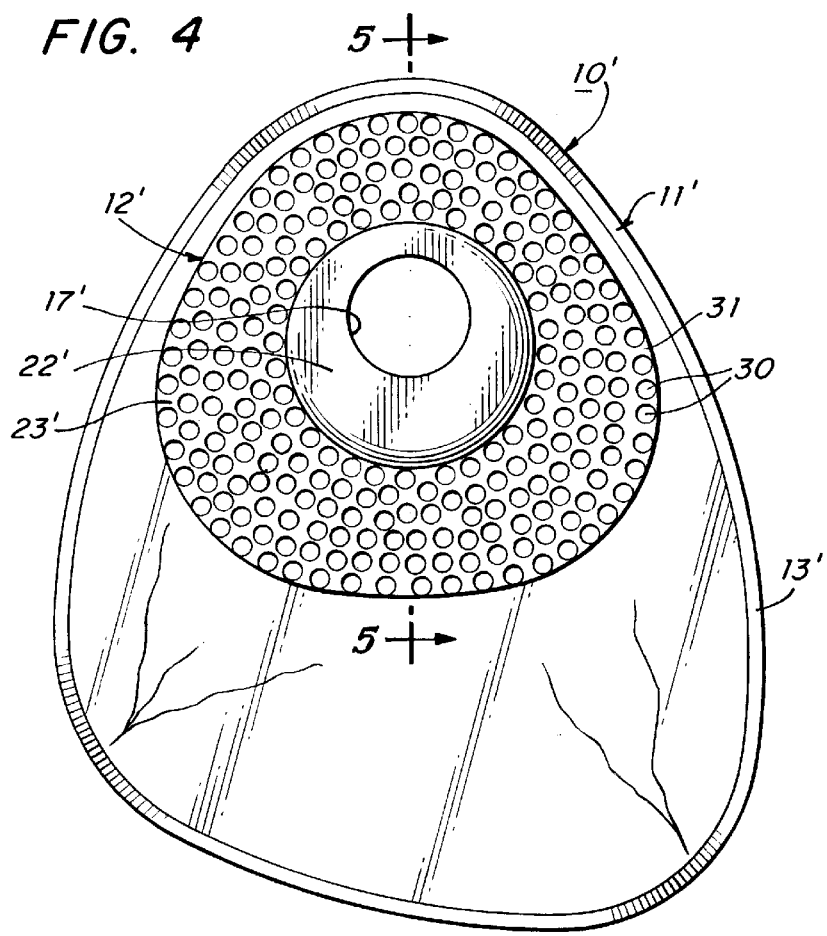
FIG. 4 is a rear elevational view of an appliance constituting a second embodiment of the invention.
Figure 5:
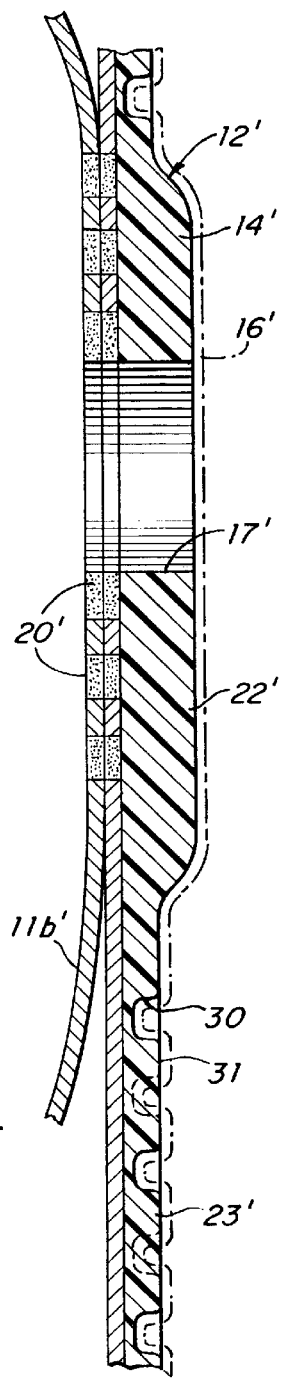
FIG. 5 is an enlarged fragmentary sectional view taken along line 5—5 of FIG. 4.
Figure 6:
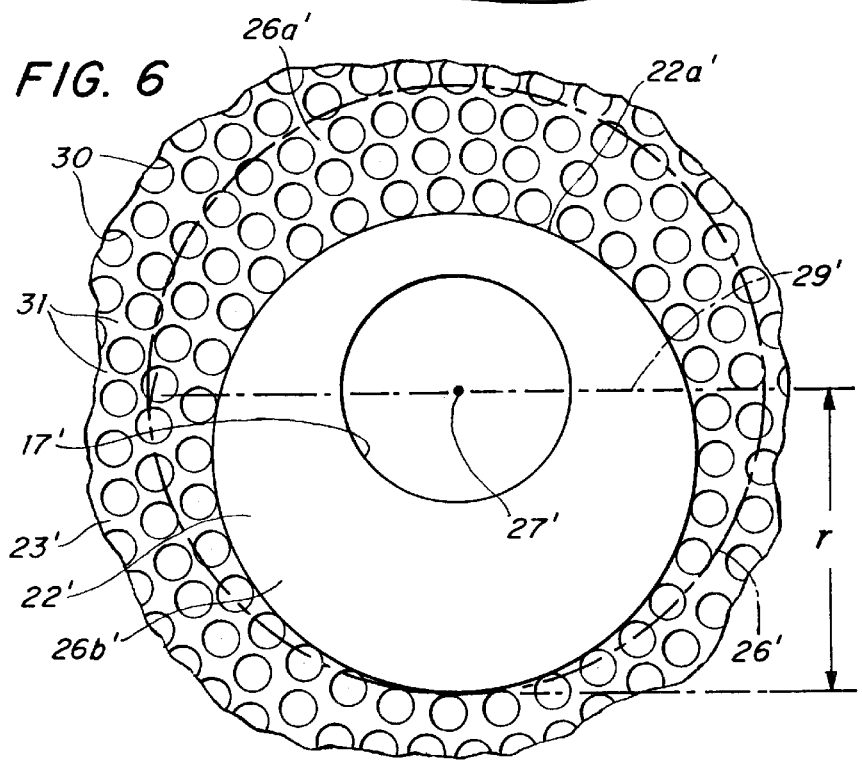
FIG. 6 is a fragmentary elevational view illustrating critical portions of the wafer in relation to a circular line of reference.

In the embodiment of FIGS. 4–6, pouch 11' is non-symmetrical in outline but is otherwise similar in construction to the pouch of the first embodiment. Wafer 12' is non-circular in outline and includes adhesive layer 14' and backing layer 15' having compositions similar to those already described. The adhesive layer 14' is contoured, having a relatively thick body portion 22' and a relatively thin peripheral portion 23', each being of the thickness ranges previously discussed. It will be noted, however, that the bodyside surface of peripheral portion 23' is embossed to provide a pattern of discrete, non-connecting depressions or recesses 30 separated and isolated from each other by ridges or shoulders 31. The depressions are preferably round in outline, although they may assume other shapes if desired, and are shown to be arranged in a non-rectilinear pattern of random appearance. The ridges 31 are flat-topped for adhesively contacting and sealingly engaging a skin surface surrounding a stoma. The flat tops of the ridges are generally coplanar with each other, and the depressions 30 are sufficiently deep so that when the wafer is in use the skin surface contacted by the adhesive layer tends to bridge the depressions.

As shown in the drawings, the bodyside surface of the relatively thick non-embossed portion 22' is smooth to insure greater sealing effectiveness with skin surfaces immediately surrounding a patient's stoma. The thickness of the non-embossed body portion 22' should be at least as great as the thickness (i.e., axial extent) of the ridges 31 of the embossed peripheral portion 23'; in the illustration given, the thickness of body portion 22' is substantially greater to enhance the moisture-absorbing capacity of the zone surrounding stoma-receiving opening 17'.

The depressions 30 are non-communicating to prevent channeling and leakage and are dimensioned and arranged to make it highly unlikely that the depressions and ridges of a replacement wafer will assume the same positions in relation to the skin as those of a wafer being replaced. In other words, when the wafer is in place, a skin surface engaged by the embossed peripheral portion primarily contacts only the ridges 31. The surface of the skin tends to bridge the depressions 30, with the result that only a fraction of the area of the embossed surface directly contacts the skin. The pattern of embossing renders it highly unlikely that only the skin areas contacted by a removed wafer will again be contacted by a fresh replacement wafer, since even slight lateral or rotational displacement in the position of the fresh wafer will bring its ridges into adhesive contact with skin surfaces not engaged by the previous wafer. The result is a wafer of enhanced skin friendliness which promotes healing, or at least avoids or reduces irritation, of the isolated skin areas underlying the depressions and which eliminates or reduces the possibilities that surface layers of skin will be stripped away as the adhesive wafer is removed.

As shown most clearly in FIG. 4, the relatively thick body portion 22' of the adhesive layer is generally circular in outline and surrounds stoma opening 17' although, as described in connection with the preceding embodiment the body portion need not be circular or annular. What is important is that opening 17' and body portion 22' are non-concentric, with the opening being above center in relation to the body portion 22'. The result is a construction in which a substantially greater quantity of adhesive barrier material is located beneath opening 17' than above it.

FIG. 6 is a diagramatic view similar to FIG. 3 and shows stoma opening 17' concentric with a line 26' defining a circular area of reference. The outer periphery of the relatively thick body portion 22' of adhesive layer 14' is indicated by line 22a'. As in the previous embodiment, it will be observed that the bulk of the thicker body portion 22' of the adhesive layer is located below the horizontal line 29' that divides the circular area of reference into semi-circular upper and lower portions 26a' and 26b'. As previously described, the lower half 26b' of the circular zone of reference therefore contains substantially more skin barrier material than upper half 26a.

Two embodiments have been disclosed for purposes of illustration, and it is to be understood that features disclosed in connection with one embodiment may be utilized with the other embodiment. For example, while the embodiment of FIGS. 1–3 is depicted with a wafer having an adhesive layer 14 with a peripheral portion having a smooth bodyside surface 14a, that surface may be embossed to provide a pattern of discrete, non-connecting depressions or recesses in the same manner as shown and described in connection with the embodiment of FIGS. 4–6. Other features may also be combined or modified without departing from the spirit and scope of the invention.

We claim:

1. A wafer for adhesively attaching an ostomy appliance to peristomal skin surfaces of a wearer, said wafer having an adhesive layer consisting of water-absorbing and water-swellable skin barrier material in which particles of one or more hydrocolloids are dispersed in a soft, pliant adhesive medium, and a flexible backing layer for attaching said wafer to a collection pouch; said adhesive layer being contoured and having a thin peripheral portion and a thick body portion; said wafer having a stoma-receiving opening surrounded by a circular area of reference having a perimeter concentric with said opening and a radius equal to the distance from the center of said opening to the lowermost limits of said thick body portion; said circular area of reference including semicircular upper and lower halves wherein said lower half contains a greater quantity of skin barrier material than said upper half.

2. The wafer of claim 1 in which said thick body portion of said adhesive layer surrounds said stoma-receiving opening.

3. The wafer of claim 2 in which said thick body portion of said adhesive layer has a circular periphery; said stoma-receiving opening having its center spaced above the center of the circle defining the periphery of said body portion.

4. The wafer of claim 1 in which said thick body portion of said adhesive layer is crescent-shaped and is located entirely below and to the sides of said stoma-receiving opening.

5. The wafer of claims 1, 2 or 4 in which said semicircular lower half of said circular area of reference contains at least 10% more skin barrier material than said upper half.

6. The wafer of claim 1, 2 or 4 in which said thin peripheral portion of said adhesive layer has a bodyside surface thereof embossed to provide a pattern of discrete, non-connecting depressions separated and isolated from each other by skin-contacting ridges dimensioned and arranged so that a skin surface engaged by said embossed surface primarily contacts only said ridges of said adhesive layer.

7. The wafer of claim 6 wherein said ridges have flat and co-planar skin-contacting surface portions.

8. The wafer of claim 6 wherein said depressions are arranged in a non-rectilinear pattern of random appearance.

9. The wafer of claim 7 wherein at least some of said depressions are round in outline.

10. The wafer of claim 1 wherein said backing layer is gas-pervious.

11. The wafer of claim 10 wherein said backing layer comprises a porous non-woven fabric.

12. The wafer of claim 6 in which a removable protective release sheet covers the surface of said adhesive layer opposite from said backing layer.

13. The wafer of claim 12 in which said release sheet includes ridges and depressions that conform with the embossed contour of said adhesive layer.

* * * * *